(12) United States Patent
Kim

(10) Patent No.: US 11,337,915 B2
(45) Date of Patent: May 24, 2022

(54) SHAMPOO COMPOSITION FOR IMPROVING SCALP AND HAIR CONDITIONS

(71) Applicant: Moonkyu Kim, Goyang-si (KR)

(72) Inventor: Moonkyu Kim, Goyang-si (KR)

(*) Notice: Subject to any disclaimer, the term of this patent is extended or adjusted under 35 U.S.C. 154(b) by 290 days.

(21) Appl. No.: 16/691,830

(22) Filed: Nov. 22, 2019

(65) Prior Publication Data
US 2020/0297618 A1 Sep. 24, 2020

(30) Foreign Application Priority Data
Mar. 21, 2019 (KR) .......................... 10-2019-0032225

(51) Int. Cl.
*A61K 8/9789* (2017.01)
*A61K 8/64* (2006.01)
*A61K 8/92* (2006.01)
*A61Q 5/02* (2006.01)
*A61Q 5/12* (2006.01)

(52) U.S. Cl.
CPC .............. *A61K 8/9789* (2017.08); *A61K 8/64* (2013.01); *A61K 8/922* (2013.01); *A61Q 5/02* (2013.01); *A61Q 5/12* (2013.01)

(58) Field of Classification Search
CPC ...................................................... A61Q 5/02
See application file for complete search history.

(56) References Cited

FOREIGN PATENT DOCUMENTS

| JP | 2003-146844 A | 5/2003 |
|---|---|---|
| KR | 10-0581316 B1 | 5/2006 |
| KR | 10-0609210 B1 | 8/2006 |
| KR | 10-0806125 B1 | 2/2008 |
| KR | 10-0839704 B1 | 6/2008 |
| KR | 10-0963792 B1 | 6/2010 |
| KR | 10-1591962 B1 | 2/2016 |
| KR | 10-2016-0069953 A | 6/2016 |
| KR | 101743197 B1 * | 6/2017 |

OTHER PUBLICATIONS

KR-101743197-B1 translated doc (Year: 2017).*

* cited by examiner

*Primary Examiner* — Terry A McKelvey
*Assistant Examiner* — Jacob A Boeckelman
(74) *Attorney, Agent, or Firm* — Korus Patent, LLC; Seong Il Jeong

(57) ABSTRACT

The present invention relates to a composition for improving scalp and hair conditions, and more particularly to a composition for improving scalp and hair conditions, containing: an extract of ginseng, rooibos, green tea, *Phellodendri cortex, Citrus unshiu* peel, *Angelica gigas, Illicium verum*, ginger, *Cnidium officinale, Paeonia japonica* and capsaicin; and dry powder of ginseng, rooibos, green tea, *Phellodendri cortex, Citrus unshiu* peel, *Angelica gigas, Illicium verum*, ginger, *Cnidium officinale, Paeonia japonica* and capsaicin. The shampoo composition for improving scalp and hair conditions according to the present invention is advantageously safe even when used for a long period of time, prevents hair loss, dandruff, etc. through scalp cleanliness, sterilization, blood circulation and nourishing, moisturizes and nourishes the hair, gives the hair luster, and has an excellent hair conditioning effect.

1 Claim, No Drawings

SHAMPOO COMPOSITION FOR IMPROVING SCALP AND HAIR CONDITIONS

CROSS-REFERENCE TO RELATED APPLICATION

This application claims the benefit of Korean Patent Application No. 10-2019-0032225 filed on Mar. 21, 2019, which is hereby incorporated by reference herein in its entirety.

BACKGROUND

1. Technical Field

The present invention relates to a composition for improving scalp and hair conditions, and more particularly to a composition for improving scalp and hair conditions, which contains ginseng, rooibos, green tea, *Phellodendri cortex*, *Citrus unshiu* peel, *Angelica gigas*, *Illicium verum*, ginger, *Cnidium officinale*, *Paeonia japonica* and capsaicin, and thus prevents hair loss by improving scalp and hair conditions and has a hair conditioning effect.

2. Description of the Related Art

Hair is damaged by friction, heat, physical cutting, perm, discoloration, dyeing, sunlight, and the like. First, regarding hair damage caused by heat, hair expands and changes its shape while water is evaporated and dried by heat generated in a dryer during drying after hair washing, and black hair turns dark brown. In addition, bubbles begin to form in hair cortex and hair medulla, resulting in loss of hair elasticity and melting of hair cuticle.

Second, hair damaged by perm is caused by poor treatment of perm solution, an insufficient period of time during which the hair is allowed to stand, etc. If the hair becomes weak or an alkaline or an oxidizing agent remains on the hair, the denaturation of keratin proteins and the discoloration of the melanin pigment will occur.

Third, the oxidative discoloration of the melanin pigment is caused by hydrogen peroxide as a bleaching agent in addition to an alkaline agent. When the hair is repeatedly exposed to the bleaching agent for a short period of time, the hair is repeatedly swollen and softened or the hair cuticle is twisted and bent, causing damage to the hair.

Finally, hair keratin protein is damaged or denatured by infrared rays and ultraviolet rays of sunlight.

Therefore, hair conditioners have been mainly used to prevent and alleviate such hair damage. In general, however, consumers with thin hair are reluctant to use the hair conditioners, in spite of excessive defatting and hair damage after shampooing, because the hair conditioners give a sticky feeling and the excessive oil content of the hair conditioners causes the hair to sink and reduces the volume of the hair.

Meanwhile, human hair grows for three years and then falls out, and after three months, new hair is formed at that site. The human head has about 80,000 hairs, of which 70 fall out a day, and about 70 hairs that fell out three months ago newly grow, so that 80,000 hairs on the human head are always maintained.

However, busy modern people are vulnerable to various stresses. The effects of these stresses and aging are most closely associated with hair loss. In the past, hair loss was recognized to be caused by heredity, but in recent years, it has been reported that hair loss is one of the phenomena caused by aging and a big problem is that the stage of hair loss is advanced by changes in living environment.

Alopecia is known to occur mainly because the function of producing hair energy, that is, the hair energy cycle, does not work normally, resulting in energy shortage in the hair roots.

Accordingly, compositions of preventing hair loss and promoting hair growth using various natural substances have been proposed. For example, Korean Patent No. 10-0839704 discloses a composition for preventing hair loss and promoting hair growth containing *Chrysanthemum zawadskii*, a kind of wild chrysanthemum. Furthermore, Korean Patent No. 10-0581316 discloses a composition for preventing hair loss and promoting hair growth containing a mixed extract of several herbal materials, including motherwort seed, *Nardostachys chinensis*, *Chrysanthemum indicum*, peach kernel, Japanese cornlian cherry, cuscuta seed, *Schisandra chinensis*, *Atractylodes macrocephala*, pine needles and *Angelica gigas*. Korean Patent No. 10-0609210 discloses a method for producing a hair loss prevention shampoo that contains an ethanol extract of *Angelica gigas* root and burdock root, and thus has a 5α-reductase inhibitory effect by the β-sitosterol component of the *Angelica gigas* root and a blood flow improvement effect by the inulin component of burdock root. Korean Patent No. 10-0579710 discloses a shampoo composition having a hair loss prevention effect together with a dandruff prevention effect by containing the ginkgolide A, ginkgolide B and bilobalide extracted from ginkgo leaf. In addition, Korean Patent No. 10-0806125 discloses a method of producing a shampoo having hair loss prevention and hair growth promotion effects by boiling various natural herbal materials added to gold/silver water containing gold and silver dissolved therein.

However, only one kind of natural material or herbal material has no significant effect on the maximization of hair loss prevention and hair growth promotion effects, and disadvantageously has only hair loss prevention and hair growth promotion functions and lacks functions such as hair conditioning.

SUMMARY

Accordingly, the present invention has been made keeping in mind the above problems occurring in the prior art, and an object of the present invention is to provide a shampoo composition for improving scalp and hair conditions, which is used to alleviate scalp itching and promote blood circulation, thus alleviating dandruff, dead skin cells, etc. and preventing hair loss.

Another object of the present invention is to supply enough nutrition to hair, thus giving the hair luster and increasing the thickness and volume of the hair.

A shampoo composition for improving scalp and hair conditions according to the present invention for achieving the above objects may contain: an extract of ginseng, rooibos, green tea, *Phellodendri cortex*, *Citrus unshiu* peel, *Angelica gigas*, *Illicium verum*, ginger, *Cnidium officinale*, *Paeonia japonica* and capsaicin; and dry powder of ginseng, rooibos, green tea, *Phellodendri cortex*, *Citrus unshiu* peel, *Angelica gigas*, *Illicium verum*, ginger, *Cnidium officinale*, *Paeonia japonica* and capsaicin.

The dry powder may be contained in an amount of 20 to 50 parts by weight based on 100 parts by weight of the extract, and the mixing ratio between ginseng, rooibos, green tea, *Phellodendri cortex*, *Citrus unshiu* peel, *Angelica gigas*, *Illicium verum*, ginger, *Cnidium officinale*, *Paeonia*

*japonica* and capsaicin, which are the materials of the extract and the dry powder, is 0.1 to 1 wt % ginseng, 0.1 to 1 wt % rooibos, 0.1 to 1 wt % green tea, 9 to 14 wt % *Phellodendri cortex,* 9 to 14 wt % *Citrus unshiu* peel, 9 to 14 wt % *Angelica gigas,* 4 to 7 wt % ginger, 9 to 14 wt % *Cnidium officinale,* 9 to 14 wt % *Paeonia japonica,* 4 to 7 wt % capsaicin, and the remainder being *Illicium verum.*

The shampoo composition may further contain a thickener, a surfactant, olive oil, vegetable glycerin, menthol, peppermint essential oil, rosemary essential oil, silk amino acids, elastin, and collagen, in which the thickener includes polyquaternium, xanthan gum and glucamate, and the surfactant includes decylglucoside, cocobetaine and olive oil PEG-7 esters.

The shampoo composition may contain, based on 100 parts by weight of the extract, 30 to 50 parts by weight of the thickener, 300 to 400 parts by weight of the surfactant, 5 to 15 parts by weight of olive oil, 10 to 30 parts by weight of vegetable glycerin, 0.5 to 2 parts by weight of menthol, 2 to 3 parts by weight of peppermint essential oil, 2 to 3 parts by weight of rosemary essential oil, 1 to 2 parts by weight of silk amino acids, 2 to 3 parts by weight of elastin, and 2 to 3 parts by weight of collagen.

DETAILED DESCRIPTION

The present invention will be described in detail below.

The present invention provides a composition having a function of improving scalp and hair conditions, that is, scalp cleanliness, sterilization, soothing, nourishing, and blood circulation improvement, and also having a function of preventing hair loss and functions of moisturizing hair, nourishing hair, giving hair luster, and increasing the thickness and volume of hair, in which the composition contains: an extract of ginseng, rooibos, green tea, *Phellodendri cortex, Citrus unshiu* peel, *Angelica gigas, Illicium verum,* ginger, *Cnidium officinale, Paeonia japonica* and capsaicin; and dry powder of ginseng, rooibos, green tea, *Phellodendri cortex, Citrus unshiu* peel, *Angelica gigas, Illicium verum,* ginger, *Cnidium officinale, Paeonia japonica* and capsaicin.

Materials that are contained in the composition of the present invention will be described below.

First, the ginseng is rich in nutrients and serves to help the regeneration of cells. In particular, saponin contained in a large amount in the ginseng maintains protein synthesis, thereby improving the thickness and volume of hair, as well as improving scalp conditions through antibacterial action, and also exhibits a hair conditioning effect.

The term "rooibos" refers to a plant having the scientific name *Asparathus linearis.* Preferably, it refers to various dried parts (e.g., leaf, flower, stem and root) of the rooibos. More preferably, it refers to means the dried leaf of the rooibos. The rooibos has the effects of alleviating scalp itching and dryness and preventing hair loss by promoting hair circulation.

The term "green tea" refers to the dried leaf of green tea. The green tea contains polyphenol and catechin components which have antioxidant activity and also serve to alleviating scalp itching by removing scale waste and alleviating dandruff and dead skin cells and to clean the scalp and hair.

The *Phellodendri cortex* is the periderm-removed stem bark of *Phellodendron amurense Rupr* or other plant belonging to the family Rutaceae. The *Phellodendri cortex* contains alkaloid components, including berberine, palmatine, guanidine, jatrorrhizine, phyellodendrine, candicine, menisperine, and the like, bitter substances, including obakunone, obakulactone and the like, steroid substances, etc., which exhibit pharmacological effects such as antibacterial activity and anti-inflammatory activity, and enhance the immunity of the skin including the scalp. In addition, it relieves scalp itching and troubles and keeps the scalp healthy by inhibiting the activity of bacteria such as dandruff bacteria.

The *Citrus unshiu* peel is the dried peel of tangerine. The essential oil component limonene contained in the tangerine peel makes a thin layer that prevents moisture evaporation from the scalp and the hair surface, thus giving the hair luster and maintaining the hair in a moisturized state for a long time.

The *Angelica gigas* contains various organic components, such as aromatic oils, vitamins, organic acids and trace elements, which soothe the scalp and prevent hair loss by promoting blood circulation.

The *Illicium verum* cleans the scalp by reducing sebum secretion, and inhibits dead skin cells, dandruff and the like by alleviating scalp itching.

The ginger promotes blood circulation by stimulating the scalp, prevents hair loss and promotes hair growth.

The *Cnidium officinale* prevents hair loss by helping blood circulation, and is rich in protein and vitamin E, which prevent aging of the scalp. In addition, it helps hair regeneration and has the basic cleaning ability to help keep the hair clean.

The *Paeonia japonica* protects the hair from external damage, moisturizes the scalp, induces hair growth, and suppresses itching and dandruff.

The capsaicin is a pungent ingredient of red pepper. The capsaicin acts on the adrenal medulla to increase the secretion of catecholamines and promote energy metabolism, thus exhibiting antioxidant and anti-inflammatory effects, and also prevents hair loss by promoting blood circulation. As the capsaicin, any of commercially available products may be used, and an extract obtained by extracting Cheongyang red pepper ethanol may also be used.

In the present invention, the mixing ratio between the materials is preferably 0.1 to 1 wt % ginseng, 0.1 to 1 wt % rooibos, 0.1 to 1 wt % green tea, 9 to 14 wt % *Phellodendri cortex,* 9 to 14 wt % *Citrus unshiu* peel, 9 to 14 wt % *Angelica gigas,* 4 to 7 wt % ginger, 9 to 14 wt % *Cnidium officinale,* 9 to wt % *Paeonia japonica,* 4 to 7 wt % capsaicin, and the remainder being *Illicium verum,* in order to maximize the hair and scalp condition improvement effects of the shampoo composition.

The shampoo composition of the present invention contains an extract and powder of these materials. The extract that is used in the present invention may be obtained by extracting active ingredients from the materials according to various methods. For example, it is possible to use a method of extracting the materials in an extraction solvent under reflux at 60 to 90° C., a method of extracting the materials in an extraction solvent under ultrasonic irradiation at 20 to 70° C., or the like, but the extraction may be performed using any method other than the above-described method, and the extraction method is not limited to the above-described method. However, water is preferably used as the extraction solvent because only the extract is used instead of water when preparing the shampoo composition. In this case, the amount of extraction solvent used is not limited and may generally be a 5 to 30-fold weight of the materials. In addition, it is to be understood that the materials are in a dried state, a non-dried state, or a dried and crushed state.

Furthermore, the dry powder of the materials may be obtained by drying the materials and crushing the dried materials to a size of about 200 to 300 mesh.

In addition, the shampoo composition of the present invention may contain, based on 100 parts by weight of the extract, 20 to 50 parts by weight of the dry powder. If the content of the dry powder is less than 20 parts by weight, a disadvantage arises in that the shampoo composition does not exhibit a sufficient effect of improving hair and scalp conditions, and if the content of the dry powder is more than parts by weight, a disadvantage arises in that the dry powder is excessive in amount, thus reducing the foamability and use feeling of the shampoo composition.

Meanwhile, the shampoo composition may further contain a thickener, a surfactant, olive oil, vegetable glycerin, menthol, peppermint essential oil, rosemary essential oil, silk amino acids, elastin, and collagen. In this case, the thickener serves to increase the viscosity of shampoo composition, and may include one or more, preferably all, of polyquaternium, xanthan gum and glucamate. In this case, the polyquaternium is not limited in the kind thereof, and polyquaternium-4, polyquaternium-7, polyquaternium-44, etc., may all be used. The thickener may be used in an amount of 30 to 50 parts by weight based on 100 parts by weight of the extract. When polyquaternium, xanthan gum and glucamate are all used as the thickener, these may be used at a weight ratio of 1:0.1 to 0.2:3 to 4.

The surfactant serves to impart detergency, and may include one or more, preferably all, of decylglucoside, cocobetaine and olive oil PEG-7 esters, which are natural surfactants. The surfactant may be used in an amount of 300 to 400 parts by weight based on 100 parts by weight of the extract. When decylglucoside, cocobetaine and olive oil PEG-7 esters are all used as the surfactant, these may be used at a weight ratio of 1:0.3 to 0.5:0.02 to 0.05.

The olive oil is used as a moisturizer and an antioxidant, and serves to moisturize the scalp and hair. The olive oil may be used in an amount of 5 to 15 parts by weight based on 100 parts by weight of the extract.

The vegetable glycerin, a natural moisturizing factor, serves to moisturize and smooth the hair and scalp. The vegetable glycerin may be used in an amount of 10 to 30 parts by weight based on 100 parts by weight of the extract.

The menthol serves to impart cooling or refreshing sensation to the scalp immediately and consistently. The menthol may be used in an amount of 0.5 to 2 parts by weight based on 100 parts by weight of the extract.

The peppermint essential oil also serves to impart refreshing sensation and has a skin soothing effect. The peppermint essential oil may be used in an amount of 2 to 3 parts by weight based on 100 parts by weight of the extract.

The rosemary essential oil helps hair growth and nourishes the hair roots. The rosemary essential oil may be used in an amount of 2 to 3 parts by weight based on 100 parts by weight of the extract.

Regarding the silk amino acids, when silk cocoon (silk protein) is hydrolyzed, a peptide composed of two or more free amino acid or amino acid molecules bound to each other is formed. The amino acids and peptides thus formed are collectively called silk amino acid, and are light yellow fine powder. The silk amino acids include eight essential amino acids (valine, isoleucine, leucine, threonine, lysine, methionine, phenylalanine, and tryptophan) and ten nonessential amino acids. These silk amino acids are very similar to human skin proteins, and thus are easily absorbed into the skin and also have excellent effects of regenerating and nourishing the skin. In addition, these silk amino acids smooth the skin and strengthen the skin barrier, thus protecting the scalp and hair from UV rays or external harmful environments. The silk amino acids may be used in an amount of 1 to 2 parts by weight based on 100 parts by weight of the extract.

The elastin provides scalp moisturizing and conditioning effects. The elastin may be used in an amount of 2 to 3 parts by weight based on 100 parts by weight of the extract.

The collagen promotes skin regeneration, hydrates and nourishes the skin, and protects the scalp and hair from external stimuli. The collagen is not limited in the kind thereof, and for example, marine collagen may be used. The collagen may be used in an amount of 2 to 3 parts by weight based on 100 parts by weight of the extract.

As described above, the shampoo composition of the present invention is advantageously safe even when used for a long period of time, prevents hair loss, dandruff, etc. through scalp cleanliness, sterilization, blood circulation and nourishing, moisturizes and nourishes the hair, gives the hair luster, and has an excellent hair conditioning effect.

In addition, the shampoo composition of the present invention may further contain, in addition to the above-described components, a conventional hair loss prevention component, hair growth component, anti-dandruff component, scalp itching prevention component, etc., which may be applied to shampoo compositions, and the kinds and contents of these conventional components are not limited.

In addition, the shampoo composition of the present invention may further contain an extract of *Litchi chinensis* seed. The extract of *Litchi chinensis* seed may be contained in an amount of 2.5 parts by weight based on 100 parts by weight of the extract.

The present invention will be described in detail below with reference to specific examples.

Example 1

First, a sample was prepared, which included 0.5 g of ginseng, 0.5 g of rooibos, 0.5 g of green tea, 10 of *Phellodendri cortex*, 10 g of *Citrus unshiu* peel, 10 g of *Angelica gigas*, 25 g of *Illicium verum*, 5 g of ginger, 10 g of *Cnidium officinale*, 10 g of *Paeonia japonica* and 5 g of capsaicin. Then, the sample was added to a 5-fold weight of water and extracted under reflux at 90° C. for 3 hours to obtain an extract. Meanwhile, a sample including 0.5 g of ginseng, 0.5 g of rooibos, 0.5 g of green tea, 10 g of *Phellodendri cortex*, 10 g of *Citrus unshiu* peel, 10 g of *Angelica gigas*, 25 g of *Illicium verum*, 5 g of ginger, 10 g of *Cnidium officinale*, 10 g of *Paeonia japonica* and 5 g of capsaicin was prepared and crushed to a size of 200 mesh to obtain dry powder. In this case, the ginseng, rooibos, green tea, *Phellodendri cortex*, *Citrus unshiu* peel, *Angelica gigas*, *Illicium verum*, ginger, *Cnidium officinale* and *Paeonia japonica* were all prepared in a dry state, and the capsaicin used was reagent-grade pure capsaicin (Aldrich's product).

6 g of the dry powder was added to 20 g of the extract and sufficiently mixed by heating at 60° C. for 3 minutes, and then 1.8 g of polyquaternium-44, 0.3 g of xanthan gum, 6 g of glucamate, 50 g of decylglucoside, 20 g of cocobetaine, 2 g of olive oil PEG-7 esters, 2 g of olive oil, 4 g of vegetable glycerin, 0.5 g of peppermint essential oil, 0.5 g of rosemary essential oil, 0.2 g of menthol, 0.3 g of silk amino acids, 0.5 g of marine elastin, and 0.5 g of marine collagen were further mixed therewith, thereby producing a shampoo composition.

Example 2

This Example was performed in the same manner as Example 1, except that 0.5 g of an extract of *Litchi chinensis* seed was further mixed when polyquaternium-44 and the like were mixed. The extract of *Litchi chinensis* seed was prepared by adding a 5-fold weight of ethanol to *Litchi chinensis* seed, extracting the *Litchi chinensis* seed at 30° C. for 5 hours, and then filtering and drying the extract.

Comparative Example 1

This Comparative Example was performed in the same manner as Example 1, except that water was mixed instead of the extract and the dry powder was not mixed.

Test Example 1

Subjects with scalp itching were selected, and using the selected subjects, a test for the compositions of the present invention was performed. The subjects were a total of 30 adult men and women (10 persons per group). The hair of each of the subjects in each group was washed once a day with the shampoo composition of each of Examples 1 and 2 and Comparative Example 1, and the results of the washing were observed and shown in Table 1 below.

For the evaluation of the effect of each composition, the degree of alleviation of itching and the sensation of stimulation were scored on a five-point scale ranging from 1 to 5, and the evaluation scores were averaged.

TABLE 1

Test results of Test Example 1

|  | Group who used Example 1 | Group who used Example 2 | Group who used Comparative Example 1 |
|---|---|---|---|
| Effect of alleviating itching | 4.0 | 4.2 | 2.2 |
| Evaluation of stimulation | 1.1 | 1.0 | 1.2 |

1: There is no effect or stimulation.
2: There is a poor effect or stimulation.
3: There is a moderate effect or stimulation.
4: There is an effect or stimulation.
5: There is a significant effect or stimulation.

As can be seen in Table 1 above, the effect of alleviating itching in the group who used Example 1 or 2 of the present invention was better than the effect of Comparative Example 1, and the degree of stimulation did not significantly differ between the groups.

Test Example 2

Subjects with hair loss were selected, and using the selected subjects, a test for the compositions of the present invention was performed. The subjects were a total of thirty 35-50-year-old adult men and women (10 persons per group). The hair of each of the subjects in each group was washed once a day with the shampoo composition of each of Examples 1 and 2 and Comparative Example 1, and the results of the washing were observed and shown in Table 2 below.

For evaluation of the effect of each composition, average daily hair loss during hair washing, visual finding and the degree of subjective symptoms improvement were scored on a five-point scale ranging from 1 to 5, and the overall improvement scores were averaged.

TABLE 2

Test results of Test Example 2

|  | Group who used Example 1 | Group who used Example 2 | Group who used Comparative Example 1 |
|---|---|---|---|
| Visual finding | 3.5 | 3.7 | 2.7 |
| Subjective symptom | 3.4 | 3.6 | 2.9 |
| Number of hair loss during hair washing | 3.3 | 3.5 | 2.8 |
| Overall improvement | 3.4 | 3.6 | 2.8 |

1: Worsened,
2: Not changed,
3: Slightly improved,
4: Moderately improved,
5: Significantly improved As can be seen in Table 2 above, visual finding, subjective symptom, the number of hair loss, and overall improvement in the groups who used Examples 1 and 2 of the present invention were all significantly better scored than those in the group who used Comparative Example 1. This suggests that Examples 1 and 2 of the present invention exhibit an excellent effect of alleviating hair loss.

Test Example 3

The use feeling of the compositions of Examples 1 and 2 were tested.

Subjects were a total of 25-35-year-old women (10 persons per group) with long straight hair or long wavy hair. The hair of each of the subjects in each group was washed once a day with the shampoo composition of each of Examples 1 and 2 and Comparative Example 1, and the results of the washing were observed and shown in Table 3 below.

TABLE 3

Test results of Test Example 3

|  | Group who used Example 1 | Group who used Example 2 | Group who used Comparative Example 1 |
|---|---|---|---|
| Detergency | 3.4 | 3.4 | 3.0 |
| Foamability | 3.5 | 3.5 | 3.6 |
| Luster | 4.1 | 4.3 | 2.9 |
| Smoothness | 4.2 | 4.3 | 2.7 |
| Hair volume | 3.9 | 4.0 | 2.7 |

1: Worsened,
2: Not changed,
3: Slightly improved,
4: Moderately improved,
5: Significantly improved As can be seen in Table 3 above, detergency, luster, smoothness and hair volume in the groups who used Examples 1 and 2 of the present invention were significantly better scored than those in the group who used Comparative Example 1. In addition, foamability did not significantly differ between the groups.

As can be seen through the above-described Examples, it could be confirmed that the shampoo composition according to the present invention alleviates itching, dandruff, etc., prevents hair loss, and has excellent hair and scalp conditioning effects.

As described above, the shampoo composition for improving scalp and hair conditions according to the present invention advantageously is safe even when used for a long period of time, prevents hair loss, dandruff, etc. through scalp cleanliness, sterilization, blood circulation and nourishing, moisturizes and nourishes the hair, gives the hair luster, increases the volume of hair, and has an excellent hair conditioning effect.

Although the present invention has been described with reference to the limited embodiments and drawings, the present invention is not limited by them, and it will be apparent that those skilled in the art may make various modifications and alterations within the technical spirit of the present invention and a range equivalent to the attached claims.

What is claimed is:

1. A shampoo composition for improving scalp and hair conditions, the shampoo composition comprising:
    100 parts by weight of an extract of ginseng, rooibos, green tea, *Phellodendri cortex*, *Citrus unshiu peel, Angelica gigas, Illicium verum*, ginger, *Cnidium officinale, Paeonia japonica* and capsaicin; 20 to 50 parts by weight of dry powder of ginseng, rooibos, green tea, *Phellodendri cortex*, *Citrus unshiu* peel, *Angelica gigas, Illicium verum*, ginger, *Cnidium officinale, Paeonia japonica* and capsaicin; 30 to 50 parts by weight of a thickener; 300 to 400 parts by weight of a surfactant; 5 to 15 parts by weight of olive oil; 10 to 30 parts by weight of vegetable glycerin; 0.5 to 2 parts by weight of menthol; 2 to 3 parts by weight of peppermint essential oil; 2 to 3 parts by weight of rosemary essential oil; 1 to 2 parts by weight of silk amino acids; 2 to 3 parts by weight of elastin; 2 to 3 parts by weight of collagen; and 2.5 parts by weight of an extract of *Litchi chinensis* seed;
    wherein a mixing ratio between ginseng, rooibos, green tea, *Phellodendri cortex*, *Citrus unshiu* peel, *Angelica gigas, Illicium verum*, ginger, *Cnidium officinale, Paeonia japonica* and capsaicin, which are the materials of the extract and the dry powder, is 0.1 to 1 wt % ginseng, 0.1 to 1 wt % rooibos, 0.1 to 1 wt % green tea, 9 to 14 wt % *Phellodendri cortex*, 9 to 14 wt % *Citrus unshiu* peel, 9 to 14 wt % *Angelica gigas,* 4 to 7 wt % ginger, 9 to 14 wt % *Cnidium officinale,* 9 to 14 wt % *Paeonia japonica,* 4 to 7 wt % capsaicin, and the remainder being *Illicium verum;*
    wherein the thickener comprises polyquaternium, xanthan gum and glucamate; and
    wherein the surfactant comprises decylglucoside, cocobetaine and olive oil PEG-7 esters.

* * * * *